(12) United States Patent
Asefa et al.

(10) Patent No.: US 11,547,680 B2
(45) Date of Patent: Jan. 10, 2023

(54) BENZALKONIUM-EMBEDDED MESOSTRUCTURED SILICA COMPOSITIONS AND USES OF SAME

(71) Applicant: RUTGERS, THE STATE UNIVERSITY OF NEW JERSEY, New Brunswick, NJ (US)

(72) Inventors: Tewodros Asefa, Kendall Park, NJ (US); Viktor Dubovoy, Piscataway, NJ (US); Anjani Ganti, King of Prussia, PA (US); Jeffrey M. Boyd, Highland Park, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 17/047,421

(22) PCT Filed: May 1, 2019

(86) PCT No.: PCT/US2019/030215
§ 371 (c)(1),
(2) Date: Oct. 14, 2020

(87) PCT Pub. No.: WO2019/213270
PCT Pub. Date: Nov. 7, 2019

(65) Prior Publication Data
US 2021/0137855 A1    May 13, 2021

Related U.S. Application Data

(60) Provisional application No. 62/665,146, filed on May 1, 2018.

(51) Int. Cl.
| | | |
|---|---|---|
| *A61K 31/14* | (2006.01) |
| *A61P 31/04* | (2006.01) |
| *A01N 25/12* | (2006.01) |
| *A01N 33/12* | (2006.01) |
| *A61K 9/00* | (2006.01) |
| *A61K 9/16* | (2006.01) |
| *A61K 31/045* | (2006.01) |
| *A61K 31/07* | (2006.01) |
| *A61K 31/192* | (2006.01) |
| *A61K 31/351* | (2006.01) |
| *A61K 31/519* | (2006.01) |
| *A61K 31/522* | (2006.01) |
| *A61K 31/573* | (2006.01) |
| *A61K 31/593* | (2006.01) |
| *A61K 31/60* | (2006.01) |
| *A61K 31/7056* | (2006.01) |
| *A61K 45/06* | (2006.01) |

(52) U.S. Cl.
CPC .............. *A61K 31/14* (2013.01); *A01N 25/12* (2013.01); *A01N 33/12* (2013.01); *A61K 9/0014* (2013.01); *A61K 9/1611* (2013.01); *A61K 31/045* (2013.01); *A61K 31/07* (2013.01); *A61K 31/192* (2013.01); *A61K 31/351* (2013.01); *A61K 31/519* (2013.01); *A61K 31/522* (2013.01); *A61K 31/573* (2013.01); *A61K 31/593* (2013.01); *A61K 31/60* (2013.01); *A61K 31/7056* (2013.01); *A61K 45/06* (2013.01); *A61P 31/04* (2018.01)

(58) Field of Classification Search
CPC ........................... A61K 31/14; A61K 47/6923
See application file for complete search history.

(56) References Cited

U.S. PATENT DOCUMENTS

| | | | |
|---|---|---|---|
| 2006/0018966 A1 * | 1/2006 | Lin ...................... | A61K 9/2081 514/358 |
| 2012/0328682 A1 | 12/2012 | Bardwell et al. | |
| 2014/0212479 A1 | 7/2014 | Zeinelden | |
| 2018/0105430 A1 | 4/2018 | Carnes et al. | |
| 2019/0111133 A1 | 4/2019 | Karathanasis et al. | |

FOREIGN PATENT DOCUMENTS

WO    WO-2016145335 A1 *    9/2016    ............. A61K 33/00

OTHER PUBLICATIONS

Stefan et al (Medical Research Journal, 2021, vol. 6, pp. 254-269) (Year: 2021).*
Wang et al (Abstract, 253rd ACS National Meeting and Exposition, San Francisco, CA; Apr. 2017; found in STN CAplus database) (Year: 2017).*
Zhang et al (Journal of Chemistry, 2016, vol. 2016, pp. 1-16) (Year: 2016).*

* cited by examiner

*Primary Examiner* — Mark V Stevens
(74) *Attorney, Agent, or Firm* — Saul Ewing LLP; Domingos J. Silva; Kevin T. O'Brien

(57) ABSTRACT

The present invention relates in one aspect to the discovery of novel mesoporous silica nanoparticles (MSNs) templated around and comprising benzalkonium chloride (BAC). In certain embodiments, the BAC-SiO₂ mesoporous nanoparticles are capable of sustained release of BAC under acidic conditions, thereby acting as a long release antimicrobial agent. In other embodiments, the BAC-SiO₂ mesoporous nanoparticles can be incorporated into a variety of consumer products as an antimicrobial agent additive, including for example, but not limited to, surgical dressings, bandages, deodorants, soaps, facial cleansers and industrial cleaners.

20 Claims, 10 Drawing Sheets

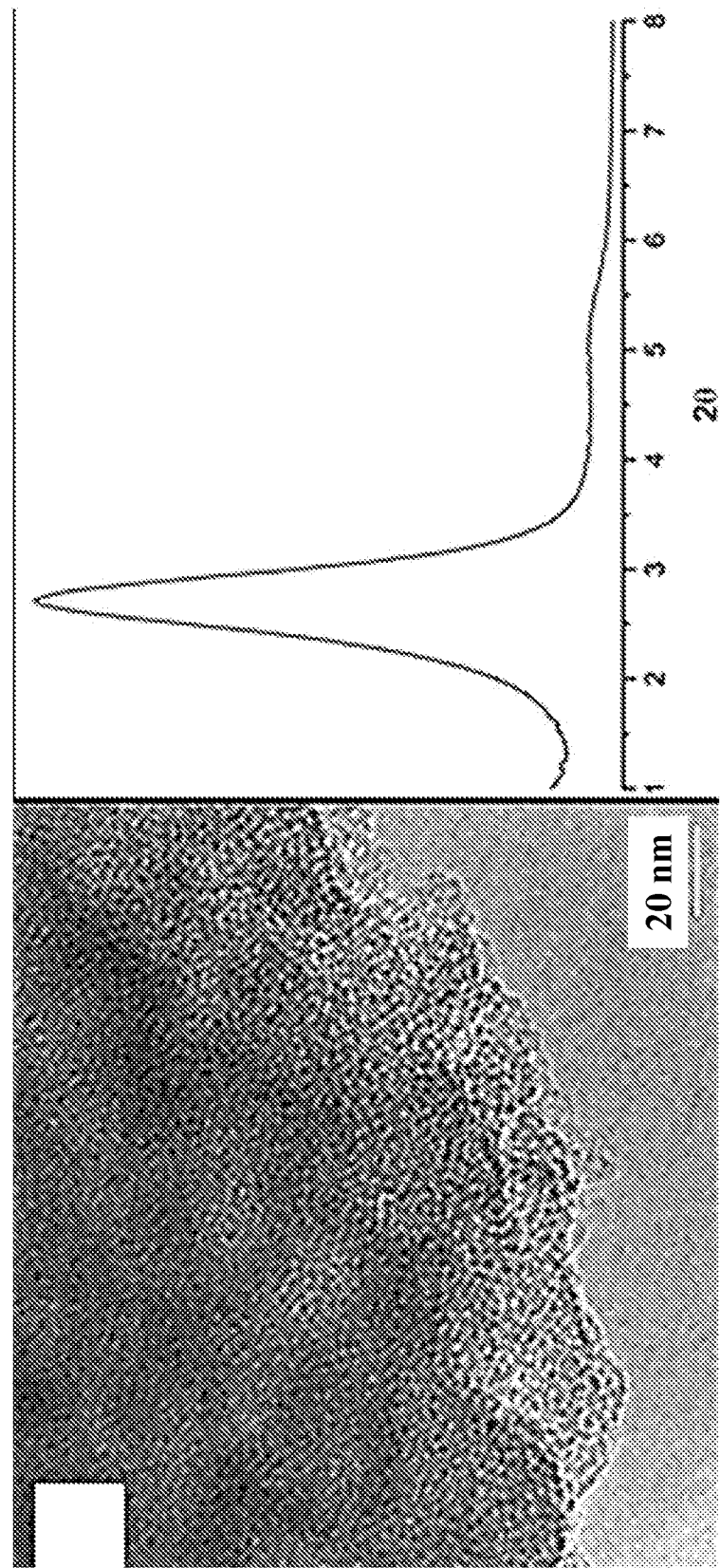

BENZALKONIUM-EMBEDDED MESOSTRUCTURED SILICA COMPOSITIONS AND USES OF SAME

CROSS-REFERENCE TO RELATED APPLICATIONS

The present application is a 35 U.S.C. § 371 national phase application from, and claims priority to, PCT International Patent Application No. PCT/US2019/030215, filed May 1, 2019, which claims priority under 35 U.S.C. § 119(e) to U.S. Provisional Application No. 62/665,146, filed May 1, 2018, all of which are incorporated herein by reference in their entireties.

STATEMENT REGARDING FEDERALY SPONSORED RESEARCH OR DEVELOPMENT

This invention was made with Government support under Grant Number AI139100 awarded by the National Institutes of Health. The Government has certain rights in this invention.

BACKGROUND OF THE INVENTION

Mesoporous silica nanoparticles (MSNs) have attracted much interest in fields such as catalysis, drug delivery systems (DDS), sensing, environmental remediation, and nanoelectronics, due to their unique structures, morphologies and properties (e.g., high surface area, uniform pores, large pore volumes, and tunable pore sizes). Since the first report of drug delivery systems based on MSNs in 2001, research on biomedical applications of MSNs has increased exponentially each year. MSNs have demonstrated significant advantages over traditional nano-based formulations in the potential treatment of diabetes, inflammation, and cancer therapy, for example.

MSNs are typically synthesized with "inert" structure directing agents (SDAs), commonly referred to as soft templates. The SDAs are subsequently removed to yield porous structures suitable for surface modification and drug loading. Various active molecules (e.g., corrosion inhibitors, antitumor drugs, and antimicrobial agents) have been used as templates for the synthesis of silica materials. That said, there have been few reports of MSNs for use as antibacterial agent delivery systems and even fewer that have evaluated the material beyond simple drug release kinetics.

Benzalkonium chloride (BAC) is a cationic quaternary ammonium surfactant mixture comprising different alkyl-benzyldimethylammonium chloride molecules functionalized with various hydrocarbon chain lengths. BAC forms micelles in aqueous solution above the critical micelle concentration (CMC) of ca. 0.5 mM. BAC also demonstrates broad spectrum bactericidal activity by effecting cell membrane permeability, causing cytolytic leakage.

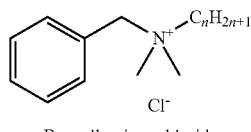

Benzalkonium chloride
n = 8, 10, 12, 14, 16, 18

There remains a need in the art for MSNs that have at least one of the following properties: can attain a high drug loading capacity for targeted drug delivery; can undergo controlled or activated release of the drug; can perform targeted delivery of the drug to specific cells, tissues and sites through certain physiological barriers; have well proven biocompatibility toward cell lines and tissues; and can be manufactured is a cost-effective and scalable manner. The present invention meets these needs.

BRIEF SUMMARY OF THE INVENTION

The present disclosure provides a composition comprising mesostructured silica particles and benzalkonium chloride. In certain embodiments, the mesostructured silica particles comprise pores. In certain embodiments, the benzalkonium chloride is embedded within the pores of the mesostructured silica particles. In certain embodiments, the silica particles are at least one selected from silica nanoparticles and/or silica microparticles.

The present disclosure further provides a method of making certain compositions described herein. In certain embodiments, the method comprises heating an aqueous solution comprising BAC, a base and a silica precursor. In certain embodiments, the method comprises collecting the mesostructured silica particles through at least one method selected from filtering the solution and/or centrifuging the solution.

BRIEF DESCRIPTION OF THE FIGURES

For the purpose of illustrating the invention, depicted in the drawings are certain embodiments of the invention. However, the invention is not limited to the precise arrangements and instrumentalities of the embodiments depicted in the drawings.

FIG. 4C is a high resolution tunneling electron microscope (TEM) image of calcined mesoporous silica fabricated through methods according to an embodiment of the invention.

FIG. 4D is a small-angle X-ray diffraction (SAXRD) pattern of calcined mesoporous silica.

DETAILED DESCRIPTION OF THE INVENTION

Figure 1:
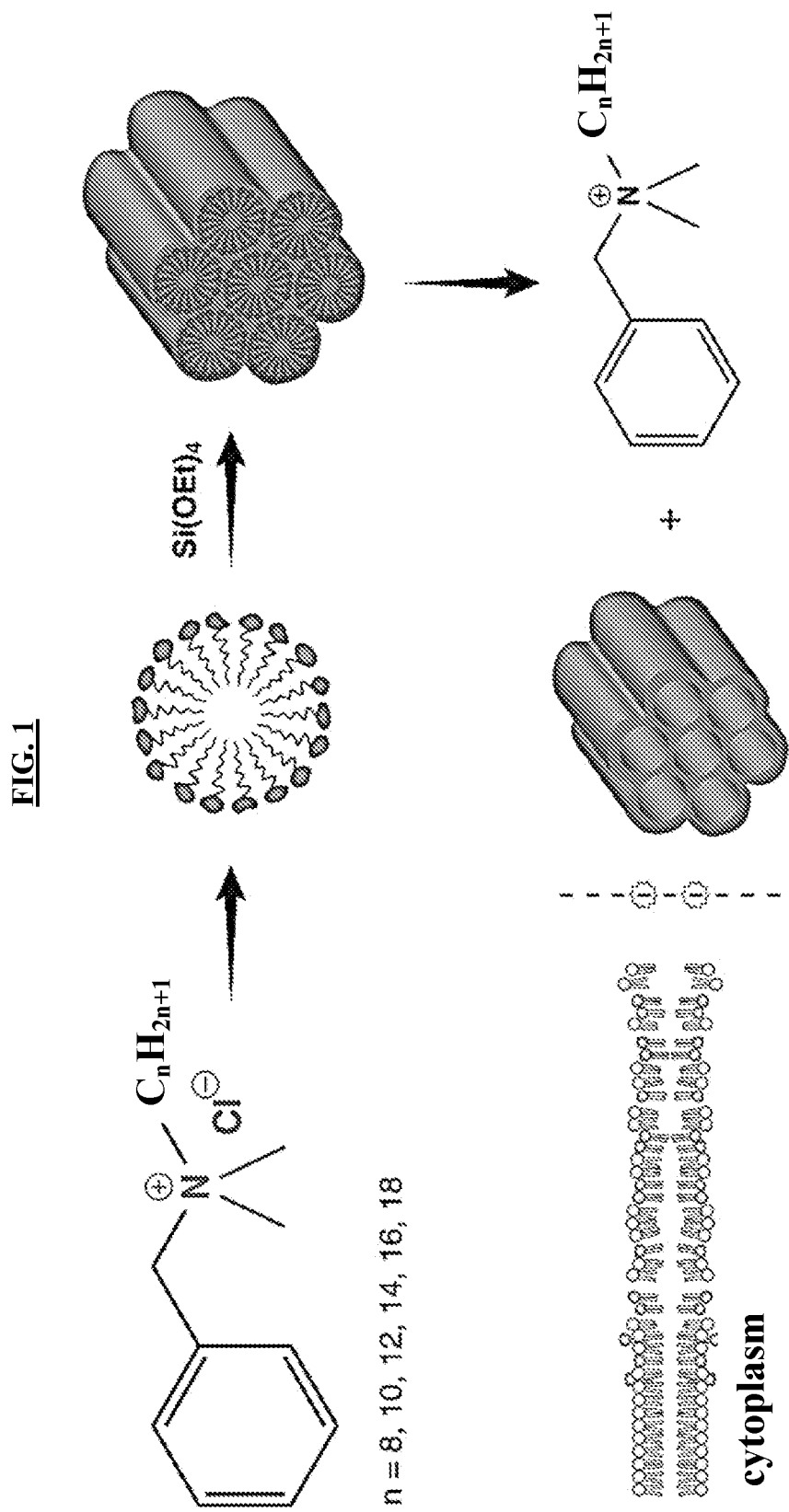
FIG. 1 is a schematic illustration of the synthetic procedure, drug release, and antimicrobial mode of action for benzalkonium chloride (BAC) templated mesoporous silica nanoparticles (MSNs) according to an embodiment of the invention.

The present invention relates to the discovery of novel mesostructured silica particles templated around and comprising benzalkonium chloride (BAC). In certain embodiments, the BAC-SiO$_2$ mesostructured particles are capable of providing sustained release of BAC under acidic conditions, thereby acting as a long-term release antimicrobial agent. In other embodiments, the BAC-SiO$_2$ mesostructured particles can be incorporated into a variety of consumer products as an antimicrobial agent additive, including but not limited to, surgical dressings, bandages, deodorants, soaps, facial cleansers and industrial cleaners.

Compositions

In one aspect, the invention provides a composition comprising mesostructured silica particles and BAC, wherein the mesostructured silica particles comprise pores and wherein the BAC is embedded within the pores of the mesostructured silica particles. In certain embodiments, the mesostructured silica particles are mesostructured silica nanoparticles or mesostructured silica microparticles.

In certain embodiments, the composition comprises more than about 1% (w/w) BAC, more than about 10% (w/w) BAC, or more than about 30% (w/w) BAC. In other embodiments, the composition comprises about 10% to about 50% (w/w) BAC, about 20% to about 40% (w/w) BAC, or about 30% to about 40% (w/w) BAC. In other embodiments, the composition comprises about 34-40% (w/w) BAC. In yet other embodiments, the composition comprises more than about 50% (w/w) BAC.

In certain embodiments, the composition further comprises at least one swelling agent. In other embodiments, the swelling agent is any hydrophobic molecule having at least 6 atoms (such as for example 6 carbon atoms), capable of expanding the volume of a BAC micelle. In yet other embodiments, the at least one swelling agent is at least one compound selected from the group consisting of 1,3,5-trimethylbenzene (TMB), polypropylene glycol) (PPG), decane, octane, 1,3,5-triisopropylbenzene, and hexane. In yet other embodiments, incorporation of the at least one swelling agent yields a mesostructured silica particle having a larger average pore size than a mesostructured silica particle of the invention that does not comprise the at least one swelling agent.

In another aspect, the invention provides a composition comprising mesoporous silica particles wherein the BAC has been released/removed from the mesostructured silica particles. In certain embodiments, the composition comprises mesoporous silica particles having a surface area greater than about 1,000 m$^2$/g. In other embodiments, the composition comprises mesoporous silica particles having a surface area of about 1,000 m$^2$/g to about 2,000 m$^2$/g. In other embodiments, the composition comprises mesoporous silica particles having a surface area greater than about 1,250 m$^2$/g. In yet other embodiments, the composition comprises mesoporous silica particles having a surface area of about 1,300 m$^2$/g to about 1,750 m$^2$/g. In yet other embodiments, the composition comprises mesoporous silica particles having a surface area of about 1,500 m$^2$/g.

In certain embodiments, the mesoporous silica comprises mesopores having an average diameter of about 10 Å to about 200 Å. In other embodiments, the mesoporous silica comprises mesopores having an average diameter of about 20 Å to about 100 Å. In yet other embodiments, the mesoporous silica comprises mesopores having an average diameter of about 30 Å to about 50 Å.

In certain embodiments, the mesoporous silica comprises mesopores having an average volume of about 0.25 cm$^3$/g to about 0.75 cm$^3$/g. In certain embodiments, the mesoporous silica comprises mesopores having an average volume of about 0.50 cm$^3$/g. In certain embodiments, the mesoporous silica comprises mesopores having an average volume of about 0.56 cm$^3$/g.

In certain embodiments, the mesoporous silica particles have an average diameter of about 50 nm to about 1,000 nm, or any range therebetween. In other embodiments, the mesoporous silica particles have an average diameter of about 50 nm to about 500 nm. In yet other embodiments, the mesoporous silica particles have an average diameter of about 200 nm to about 2,000 nm.

In certain embodiments, the mesostructured silica particle composition of the invention releases BAC when placed in solution. In other embodiments, the mesostructured silica particle composition of the invention releases less than about 3% BAC over a period of 3 days in a phosphate buffered saline (PBS) solution at pH 7.4. In yet other embodiments, the mesostructured silica particle composition of the invention releases more than about 7% BAC over a period of 3 days in an aqueous solution of pH 4.0. In yet other embodiments, the mesostructured silica particle composition of the invention is capable of sustained release of BAC over a period of greater than 3 days at pH 4.0. Without intending to be limited to any particular theory, the composition of the invention releases BAC at a faster rate in acidic solution, because the BAC is electrostatically bound to silanol sites in the mesostructured silica particles. At lower pH, the BAC is liberated through ion exchange with H$^+$ ions as well as due to a reduction in available silanol sites due to acid catalyzed condensation of silanol groups.

In certain embodiments, the mesostructured silica particle composition of the invention is capable of providing targeted release of BAC based on pH. In other embodiments, the composition does not release appreciable amounts of BAC in environments wherein the pH is neutral (pH 6-8), but does release BAC in acidic environments (pH 1-5).

In certain embodiments, the composition is an antimicrobial composition. In other embodiments, the composition is an antibacterial composition. In yet other embodiments, the composition is capable of killing Gram-positive and/or Gram-negative human bacterial pathogens. In certain embodiments, the composition is at least equally effective at killing bacterial pathogens as pure BAC on an equimolar basis. In yet other embodiments, the compositions is an antiviral composition. In yet other embodiments, the composition is an antifungal composition.

In certain embodiments, the composition is a pharmaceutically acceptable composition. In other embodiments, the composition is a pharmaceutically acceptable composition formulated for topical administration. In yet other embodiments, the composition further comprises one or more pharmaceutically acceptable salts or carriers. In yet other embodiments, the composition is a pharmaceutically acceptable composition incorporated into one or more selected from the group consisting of a wound dressing (e.g., a bandage, a patch, a graft, a surgical dressing, gauss), a lotion, an ointment, a gel, a powder, a spray (e.g., an aerosolized spray) and a solution. In other embodiments, the solution can be an aqueous solution or an anhydrous solution. In certain embodiments, the composition can be incorporated into at least one product selected from a soap, a facial cleanser, a shampoo, a toothpaste, an eye drop, an ear drop, a nasal spray or drop, a hand wipe, an antiseptic spray, a throat lozenge, a mouthwash, and a spermicide.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations can, for example, comprise from about 1% to about 10% (w/w) active ingredient, although the concentration of the active ingredient can be as high as the solubility limit of the active ingredient in the solvent. Formulations for topical administration can further comprise one or more of the additional ingredients described herein.

In certain embodiments, the composition is formulated for use as a cleaning agent. In other embodiments, the composition is formulated for use as a disinfecting agent. In certain embodiments, the composition is formulated as part of an antimicrobial coating. In other embodiments, the composition is formulated as part of an antifungal agent. In yet other embodiments, the composition is formulated as part of an antiviral agent. In yet other embodiments, the composition is formulated as part of a preserving agent or a bacteriostatic agent.

In certain embodiments, the composition further comprises at least one anionic surfactant or cationic surfactant. In other embodiments, the composition is resistant to degradation or deactivation in the presence of charged species, such as but not limited to anionic surfactants and cationic surfactants. Without intending to be limited to any particular theory, by embedding the BAC within the pores of mesostructured silica particles, the BAC is not exposed to surfactants that would normally deactivate or otherwise render useless unprotected BAC.

In certain embodiments, the composition further comprises at least one pharmaceutical agent besides the BAC. In other embodiments, the at least one pharmaceutical agent is at least one selected from the group consisting of an analgesic agent, an anti-inflammatory agent, an antimicrobial agent, an antiviral agent, an antifungal agent, an antipruritic, an antiperspirant, a sunblocking agent, a vitamin, an NSAID, a skin cleanser, a disinfectant, a corticosteroid, a protein, a peptide and a hormone. In other embodiments, the at least one pharmaceutical agent is at least one selected from the group consisting of ethanol, folic acid, salicylic acid, benzoic acid, hydrocortisone, vitamin A and derivatives and analogues thereof, vitamin D and derivatives and analogues thereof, clindamycin, mupirocin, acyclovir, and clobetasol propionate. In yet other embodiments, the at least one pharmaceutical agent and the at least one swelling agent are the same compound.

Methods

In another aspect, the invention provides methods of making a composition of the invention.

In certain embodiments, the method comprises contacting an aqueous solution comprising benzalkonium chloride (BAC) and a base with a silica precursor material to form a first system. In certain embodiments, the method comprises heating the first system comprising BAC, the base and the silica precursor material. In certain embodiments, the method comprises separating the mesostructured silica particles from the first system. In other embodiments, the mesostructured silica particles are separated from the first system by filtering or centrifuging the first system, to collect the mesostructured silica particles.

In certain embodiments, the first system is heated to about 80° C. In other embodiments, the first system is heated for about 5 min to about 72 h.

In certain embodiments, the collected mesostructured silica particles are dried after being separated via filtration or centrifugation.

In certain embodiments, the base is at least one base selected from the group consisting of ammonium hydroxide ($NH_4OH$), $Na_2CO_3$, $(Et)_3NEt_3$, lysine, NaOH, and KOH. In other embodiments, the base is any source of hydroxide ion ($OW$) known in the art.

In certain embodiments, the silica precursor material is any silicon oxide material wherein each silicon atom is covalently bound to four oxygen atoms. In other embodiments, the silica precursor material is at least one selected from the group consisting of tetraethyl orthosilicate (TEOS), sodium silicate, tetramethyl orthosilicate (TMOS), tetrapropyl orthosilicate (TPOS), tetrabutyl orthosilicate (TBOS), silicic acid, sodium silicate, and ammonium hexafluorosilicate ($(NH_4)_2SiF_6$).

In certain embodiments, the silica precursor is contacted with the aqueous solution dropwise. In certain embodiments, the BAC and the silica precursor are contacted in a molar ratio of such that there are at least 10 moles of silica for every 1 mole of BAC. In other embodiments, the BAC and the silica precursor are contacted in a molar ratio of about 1:10 to about 1:100 (BAC:silica). In yet other embodiments, the BAC, the base and the silica precursor are contacted in a molar ratio of about 0.25:4:1 (BAC:base:silica). In yet other embodiments, a person of ordinary skill in the art would be able to modify the ratios of BAC, base and silica so as to arrive at a mesostructures silica particle of the invention. In certain embodiments, the aqueous solution is an alkaline solution. In other embodiments, the aqueous solution has a pH greater than about 7. In yet other embodiments, the aqueous solution has a pH greater than about 9.

In certain embodiments, the method further comprises contacting the first system with a mineralizer of silica. In other embodiments, the mineralizer is a fluoride ($F^-$) salt, such as, but not limited to (NaF). In yet other embodiments, the mineralizer is contacted with the first system in a molar ratio of less than about 5%, as compared to the silica precursor. In yet other embodiments, the mineralizer is contacted with the first system in a molar ratio of less than about 3%, as compared to the silica precursor.

Kits

The invention includes a kit comprising a composition of the invention and an instructional material for use thereof. In certain embodiments, the instructional material comprises methods of using the composition of the invention as a disinfectant.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "bacteria" means a large domain of prokaryotic microorganisms. Typically a few micrometres in length, bacteria have a wide range of shapes, ranging from spheres to rods and spirals. There are broadly speaking two different types of cell wall in bacteria, called Gram-positive and Gram-negative. Gram-positive bacteria possess a thick cell wall containing many layers of peptidoglycan and teichoic acids. Gram-negative bacteria have a relatively thin cell wall consisting of a few layers of peptidoglycan surrounded by a second lipid membrane containing lipopolysaccharides and lipoproteins.

As used herein, the terms "bacterial pathogen" or "pathogenic bacteria" mean a bacterium that causes disease. Examples of pathogenic bacteria which can be killed or otherwise impeded by the compositions of the invention include, without limitation, any one or more of (or any combination of) *Acinetobacter baumanii*, *Actinobacillus* sp., *Actinomycetes*, *Actinomyces* sp. (such as *Actinomyces israelii* and *Actinomyces naeslundii*), *Aeromonas* sp. (such as *Aeromonas hydrophila*, *Aeromonas veronii biovar sobria* (*Aeromonas sobria*), and *Aeromonas caviae*), *Anaplasma phagocytophilum*, *Alcaligenes xylosoxidans*, *Acinetobacter baumanii*, *Actinobacillus actinomycetemcomitans*, *Bacillus* sp. (such as *Bacillus anthraces*, *Bacillus cereus*, *Bacillus subtilis*, *Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae*, *Bifidobacterium* sp., *Bordetella* sp. (such as *Bordetella pertussis*, *Bordetella parapertussis*, and *Bordetella bronchiseptica*), *Borrelia* sp. (such as *Borrelia recurrentis*, and *Borrelia burgdorferi*), *Brucella* sp. (such as *Brucella abortus*, *Brucella canis*, *Brucella melintensis* and *Brucella suis*), *Burkholderia* sp. (such as *Burkholderia pseudomallei* and *Burkholderia cepacia*), *Campylobacter* sp. (such as *Campylobacter jejuni*, *Campylobacter coli*, *Campylobacter lari* and *Campylobacter fetus*), *Capnocytophaga* sp., *Cardiobacterium hominis*, *Chlamydia trachomatis*, *Chlamydophila pneumoniae*, *Chlamydophila psittaci*, *Citrobacter* sp. *Coxiella burnetii*, *Corynebacterium* sp. (such as, *Corynebacterium diphtheriae*, *Corynebacterium jeikeum* and *Corynebacterium*), *Clostridium* sp. (such as *Clostridium perfringens*, *Clostridium difficile*, *Clostridium botulinum* and *Clostridium tetani*), *Eikenella corrodens*, *Enterobacter* sp. (such as *Enterobacter aerogenes*, *Enterobacter agglomerans*, *Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae*, *Eubacterium* sp., *Francisella tularensis*, *Fusobacterium nucleatum*, *Gardnerella vaginalis*, *Gemella morbillorum*, *Haemophilus* sp. (such as *Haemophilus influenzae*, *Haemophilus ducreyi*, *Haemophilus aegyptius*, *Haemophilus parainfluenzae*, *Haemophilus haemolyticus* and *Haemophilus parahaemolyticus*, *Helicobacter* sp. (such as *Helicobacter pylori*, *Helicobacter cinaedi* and *Helicobacter fennelliae*), *Kingella kingii*, *Klebsiella* sp. (such as *Klebsiella pneumoniae*, *Klebsiella granulomatis* and *Klebsiella oxytoca*), *Lactobacillus* sp., *Listeria monocytogenes*, *Leptospira interrogans*, *Legionella pneumophila*, *Leptospira interrogans*, *Peptostreptococcus* sp., *Moraxella catarrhalis*, *Morganella* sp., *Mobiluncus* sp., *Micrococcus* sp., *Mycobacterium* sp. (such as *Mycobacterium leprae*, *Mycobacterium tuberculosis*, *Mycobacterium intracellulare*, *Mycobacterium avium*, *Mycobacterium bovis*, and *Mycobacterium marinum*), *Mycoplasm* sp. (such as *Mycoplasma pneumoniae*, *Mycoplasma hominis*, and *Mycoplasma genitalium*), *Nocardia* sp. (such as *Nocardia asteroides*, *Nocardia cyriacigeorgica* and *Nocardia brasiliensis*), *Neisseria* sp. (such as *Neisseria gonorrhoeae* and *Neisseria meningitidis*), *Pasteurella multocida*, *Plesiomonas shigelloides*. *Prevotella* sp., *Porphyromonas* sp., *Prevotella melaninogenica*, *Proteus* sp. (such as *Proteus vulgaris* and *Proteus mirabilis*), *Providencia* sp. (such as *Providencia alcalifaciens*, *Providencia rettgeri* and *Providencia stuartii*), *Pseudomonas aeruginosa*, *Propionibacterium acnes*, *Rhodococcus equi*, *Rickettsia* sp. (such as *Rickettsia rickettsia*, *Rickettsia akari* and *Rickettsia prowazekii*, *Orientia tsutsugamushi* (formerly: *Rickettsia tsutsugamushi*) and *Rickettsia typhi*), *Rhodococcus* sp., *Serratia marcescens*, *Stenotrophomonas maltophilia*, *Salmonella* sp. (such as *Salmonella enterica*, *Salmonella typhi*, *Salmonella paratyphi*, *Salmonella enteritidis*, *Salmonella cholerasuis* and *Salmonella typhimurium*), *Serratia* sp. (such as *Serratia marcesans* and *Serratia liquifaciens*), *Shigella* sp. (such as *Shigella dysenteriae*, *Shigella flexneri*, *Shigella boydii* and *Shigella sonnei*), *Staphylococcus* sp. (such as *Staphylococcus aureus*, *Staphylococcus epidermidis*, *Staphylococcus hemolyticus*, *Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equismilis*, Group D streptococci, *Streptococcus bovis*, Group F streptococci, and *Streptococcus anginosus* Group G streptococci), *Spirillum minus, Streptobacillus moniliformi, Treponema* sp. (such as *Treponema carateum, Treponema petenue, Treponema pallidum* and *Treponema endemicum, Tropheryma whippelii, Ureaplasma urealyticum, Veillonella* sp., *Vibrio* sp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Yersinia* sp. (such as *Yersinia enterocolitica, Yersinia pestis*, and *Yersinia pseudotuberculosis*) and *Xanthomonas maltophilia* among others.

As used herein, an "instructional material" includes a publication, a recording, a diagram, or any other medium of expression that can be used to communicate the usefulness of a composition or method of the invention in the kit for treating, preventing or alleviating various diseases or disorders recited herein. Optionally, or alternately, the instructional material can describe one or more methods of treating, preventing or alleviating diseases or disorders in a cell or a tissue of a mammal. The instructional material of the kit of the invention can, for example, be affixed to a container that contains the identified composition or delivery system of the invention or be shipped together with a container that contains the identified composition or delivery system. Alternatively, the instructional material can be shipped separately from the container with the intention that the instructional material and the composition be used cooperatively by the recipient.

"Mesoporous" is defined herein as having a 2D or 3D structure comprising pores ranging in diameter from 2-50 nm. In certain embodiments, the pores are interconnected and in other embodiments, the pores are not interconnected.

The term "mesostructured" as used herein means a structured material having filled or unfilled pore structural features with an average size in the range of about 1 nm to about 100 nm or about 2 nm to about 50 nm.

The term "nanoparticle" as used herein means a particle whose size is measured in nanometers (nm). It is defined as a particle that does not have a dimension >about 100 nm, such as having a size between about 1 and about 100 nm, for example, between about 10 and about 100 nm, between 10 and about 50 nm, or between about 1 and about 10 nm. Nanoparticles are effectively a bridge between bulk materials and atomic or molecular structures. A bulk material should have constant physical properties regardless of its size, but at the nano-scale this is often not the case. Size-dependent properties are observed such as quantum confinement in semiconductor particles, surface plasmon resonance in some metal particles and superparamagnetism in magnetic materials.

The term "microparticle" as used herein refers to a microscopic particle whose size is measured in micrometers (μm). Microparticle is defined as a particle that is about 100 nm to about 100 μm in size.

As used herein, the term "pharmaceutical composition" or "pharmaceutically acceptable composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable" refers to a material, such as a carrier or diluent, which does not abrogate the biological activity or properties of the compound, and is relatively non-toxic, i.e., the material can be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that can be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: APS, Advanced Photon Source; ATR, Attenuated total reflectance; BAC, benzalkonium chloride; BAC-SiO$_2$, benzalkonium chloride templated mesostructured silica nanoparticles; BET, Brunauer-Emmett-Teller; BJH, Barrett-Joyner-Halenda; CFU, colony forming units; CTAB, cetyltrimethylammonium bromide; DSC, differential scanning calorimetry; FTIR, Fourier-transform infrared; HRTEM, high-resolution transmission electron microscope; MSN, mesoporous silica nanoparticles; PBS, phosphate-buffered saline; SAXRD, small-angle X-ray diffraction; SAXS, small-angle X-ray scattering; SCTA, Sample controlled thermal analysis; SLS, static light scattering; TEOS, tetraethyl orthosilicate; TEM, transmission electron microscopy; TGA, thermogravimetric analysis; XRD, X-ray diffraction.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. Although the description herein contains many embodiments, these should not be construed as limiting the scope of the invention but as merely providing illustrations of some of the presently preferred embodiments of the invention.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application. In general, the terms and phrases used herein have their art-recognized meaning, which can be found by reference to standard texts, journal references and contexts known to those skilled in the art. Any preceding definitions are provided to clarify their specific use in the context of the invention.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Synthesis of Benzalkonium-Templated Mesostructured Silica

Reagent grade tetraethoxysilane (TEOS), BTC® 50 solution of 50% benzalkonium chloride (BAC), and 30% aqueous ammonium hydroxide (NH$_4$OH) were supplied by Sigma-Aldrich (St. Louis, Mo.), Stepan (Northfield, Ill.) and Sigma-Aldrich (St. Louis, Mo.), respectively. All materials were used as received without any further purification. Synthesis of the MSN was carried out under mildly alkaline conditions according to the molar ratio 1 TEOS:4NH$_4$OH: 0.25BAC:135H$_2$O. BAC (4.023 g), NH$_4$OH (11.40 g), and deionized water (56.7 g) were combined in a Teflon-lined autoclave, under magnetic stirring, to form a clear solution. Then, 5.076 g of TEOS was added dropwise under stirring, and the mixture was subsequently heated at 80° C. for 72 h. A fluffy, white powder was recovered after filtration, washing, and drying at 50° C. For subsequent analysis and characterization experiments, the as-synthesized sample was calcined in air at 550° C. for 6 h to remove the template.

Characterization of Benzalkonium-Templated Mesostructured Silica

ATR-FTIR Spectroscopy

Attenuated total reflectance Fourier transform infrared (ATR-FTIR) spectroscopy analysis was conducted on BAC-SiO$_2$ and lyophilized BAC samples. The ATR-FTIR spectra (650-4000 cm$^{-1}$ with 4 cm$^{-1}$ resolution) were collected using a Perkin Elmer (Waltham, Mass.) Spectrum 2000 instrument featuring a KBr beam splitter, DTGS detector and a single-bounce diamond ATR crystal.

Brunauer-Emmett-Teller (BET) Surface Area & Barrett-Joyner-Halenda (BJH) Pore Analyses Prior to N$_2$ sorption experiments, the samples were initially de-gasified for 8 h at 80° C. under a nitrogen atmosphere using a Micromeritics (Norcross, Ga.) FlowPrep 060 Sample Degas System. Nitrogen adsorption-desorption isotherms were measured on a Micromeritics (Norcross, Ga.) Tristar 3000 instrument (Norcross, Ga.). The specific surface areas were calculated by using the BET method. The pore size distributions and total pore volume were calculated from the isotherms according to the BJH method.

SLS

Aqueous size distribution was measured by the static light scattering technique. An aliquot of the fresh solution was transferred to a polystyrene cuvette prior to analysis.

SAXS

The SAXS measurements were performed at the 12-ID-B beamline of the Advanced Photon Source (APS) at Argonne National Laboratory, using 13.3 keV X-ray energy and 0.9322 Å wavelength. The SAXS data were collected with a Pilatus 2 M detector (DECTRIS Ltd.), and the cutoff energy was set as 10 keV to eliminate possible fluorescence background. The beam size with 0.1×0.2 mm$^2$ and exposure times of 1 s were used for the measurement. The sample-to-detector distance was ca. 2 m, and the scattering vector (q) range covers 0.004-0.9 A$^{-1}$. The 2-D SAXS patterns were fully corrected, reduced to 1-D intensity versus q profiles, and background subtracted, using the software package at the beamline.

TGA

The amount of BAC incorporated in the MSN was calculated by thermogravimetric analysis (TGA) using a TGA 7 Thermogravimetric Analyzer (Perkin Elmer, Waltham, Mass.) instrument. The analysis was carried out in open platinum crucibles over a temperature range of 50-550° C. at a heating rate of 10° C./min.

TEM

Sample preparation entailed suspending the sample in ethanol, dropping onto a holey copper grid, and allowed to air-dry in room temperature. The electron microscopy experiments were performed using a JEOL 2010F microscope operated at 197 kV. The spatial resolution of the microscope in the high resolution (HRTEM) mode is ~1.4 Å. The fast Fourier transform of the HRTEM images generates spots which correspond to crystallographic periodic arrangements of atomic planes. These spots were also used as filters to remove background noise from the high resolution images. All HRTEM images were analyzed using Gatan Digital Micrograph software.

DSC

Differential scanning calorimetry was conducted on a TA DSC Q20 equipped with a TA refrigerated cooling system 90

SAXRD

The x-ray scattering from the sample was obtained by use of a Bruker Vantec-500 area detector and a Bruker FR571 rotating-anode x-ray generator operating at 40 kV and 50 mA. The diffraction system was equipped with a 3-circle Azlan goniometer, but the sample was not moved during x-ray data collection. The system used 0.5 mm pinhole collimation and a Rigaku Osmic parallel-mode (e.g., primary beam dispersion less than 0.01 degree in 2θ) mirror monochromator (Cu Kα; λ=1.5418 Å). Data were collected at room temperature (20° C.) with a sample to detector distance of 26.2 cm. Spatial calibration and flood-field correction for the area detector were performed at this distance prior to data collection. The 2048×2048 pixel images were collected at the fixed detector (2θ) angle of 50° for 3 min with ω step of 0.00 deg. For the intensity versus 2θ plot, a 0.02 degree step, bin-normalized χ integration was performed on the image shown below with settings 0<2θ<13 degree and −180<χ<180 degree.

Data collection and rocking curve creation: Bruker GADDS v.4.1.51 (2015). Data display and graphics: MDI JADE7 v.7.0.6 (2004).

Drug Release Studies

Static room temperature release of BAC from the MSN was investigated at different pH conditions: 1) HCl solution at pH 4.0 and 2) phosphate-buffered saline (PBS) solution at pH 7.4. Calibration curves were plotted by measuring the UV-Vis spectroscopy of pure BAC in the corresponding solutions. Specifically, 400 mg of BAC-SiO$_2$ was suspended in 50 mL of dispersion medium. The solution was centrifuged at prefixed time intervals, and a 1 mL aliquot of the supernatant was taken using a pipette and analyzed for BAC content at λ$_{max}$ of 262 nm. The region between 240 and 280 nm exhibits three peaks in UV-Vis, which is consistent with UV-Vis of other quaternary ammonium surfactants. The analyzed supernatant was then returned to the solution. This process was repeated at different intervals of time until no further substantial release was observed. The absorption intensity was plotted as a function of time using a Lambda 850 UV/Vis Spectrometer (PerkinElmer, Waltham, Mass.).

The drug loading capacity was then computed to a value of x g/g using the following equation:

$$\text{Drug loading capacity} = \frac{\text{mass of drug in the MSNs}}{\text{mass of drug-loaded MSN}}$$

Kinetic analysis was conducted via Power law model.

$$\frac{M_t}{M_\infty} = kt^n$$

$$\rightarrow \log\frac{M_t}{M_\infty} = \log kt^n$$

$$\rightarrow \log\frac{M_t}{M_\infty} = \log k + \log t^n$$

$$\rightarrow \log\frac{M_t}{M_\infty} = \log k + n\log t$$

$$\rightarrow \log\frac{M_t}{M_\infty}(y) = \log k(\text{constant } b) + n\log t(x); [y = nx + b]$$

$M_t/M_\infty$ is a fraction of drug released at time t, k is the release rate constant and n is the release exponent. The n value is used to determine the release mechanism; n and k can be calculated from slope and intercept, respectively.

Microbiological Assays

Broth cultures were grown at 37° C. with a shake speed of 200 RPM in 250 mL flasks. Cultures of *Staphylococcus aureus* USA300 LAC and *Salmonella enterica* serovar *typhimurium* LT2 were grown for 18 hours in 75 mL of Mueller-Hinton (Sigma-Aldrich) medium. *S. enterica* and *S. aureus* were individually diluted in triplicate into flasks containing 30 mL or 100 mL of Mueller-Hinton broth to an optical density (A$_{600}$) of 0.1, respectively. Subsequently, bacteria were combined with vehicle control, BAC-SiO$_2$, BAC, or SiO$_2$. At various times, bacteria were removed from the flasks, serial diluted using sterile phosphate buffered saline, and 5 μL of each dilution was then by drop plated onto solid tryptic soy medium (MP biomedical). The plates were incubated at 37° C. for 18 hours before the number of viable bacteria were enumerated by counting the number of colony forming units (CFU).

Example 1: Synthesis of BAC-Templated Mesostructured Silica Nanoparticles

The synthesis of BAC-templated mesostructured silica nanoparticles entailed diluting appropriate amounts of BAC and NH$_4$OH using deionized water with subsequent dropwise addition of tetraethyl orthosilicate (TEOS) under stirring. The distribution of alkyl chains in the BAC was 50% C12, 30% C14, 17% C16, and 3% C18. The resulting mixture, with the composition of BAC:TEOS:NH$_4$OH:H$_2$O=0.25:1.00:4.00:150.00, was heated at 80° C. in a 125 mL autoclave for 72 h and subsequently filtered, washed with 100 mL of water, and dried in an oven at 50° C. overnight. Calcination was conducted at 550° C. for 6 h with 10° C./min.

Figure 2:
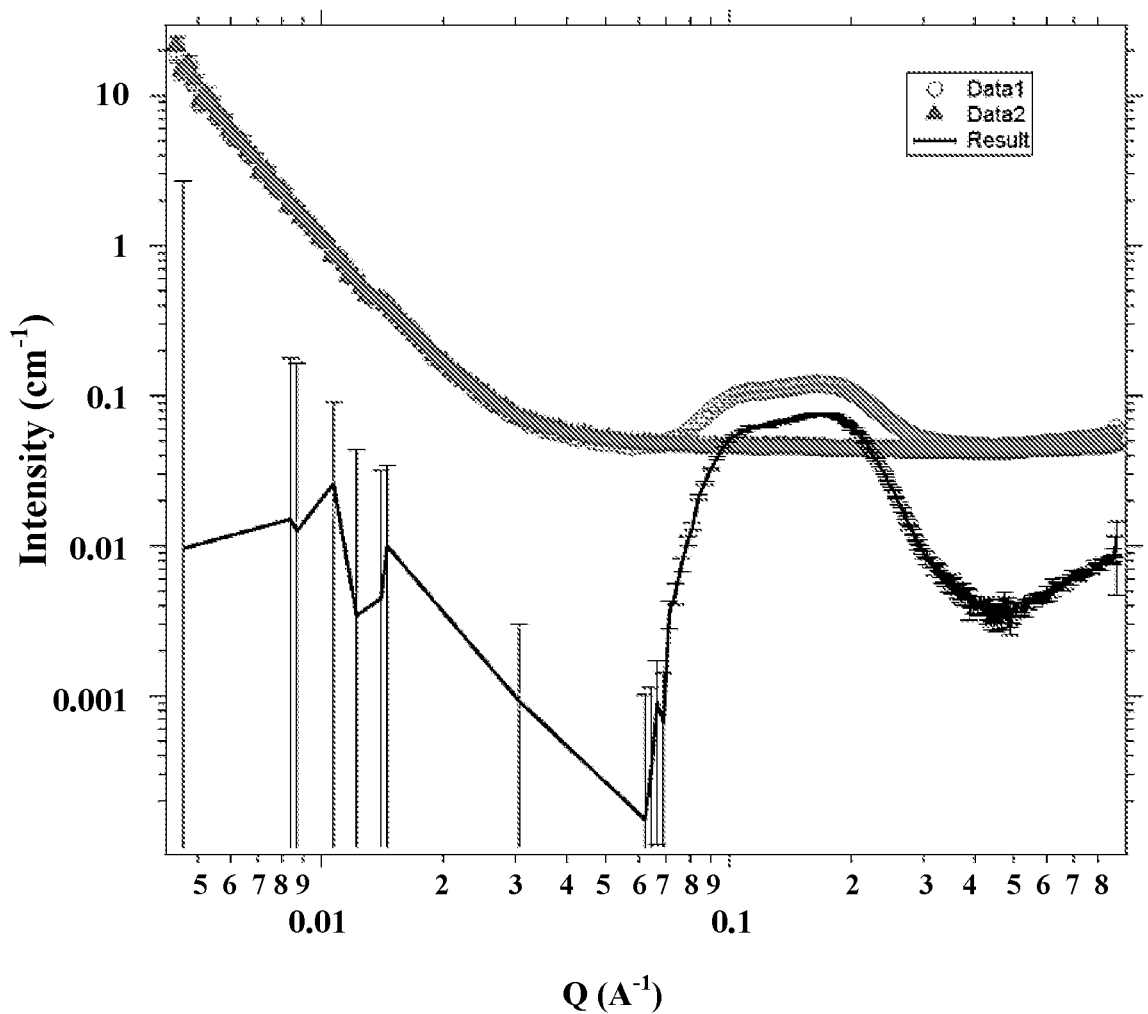
FIG. 2 is a plot showing synchrotron-SAXS measurements (Data 1) of an aqueous BAC/NH$_4$OH solution prior to the addition of tetraethoxysilane (TEOS) with its corresponding curved fit (Data 2) and the subtracted plot (Result).
Figure 3:
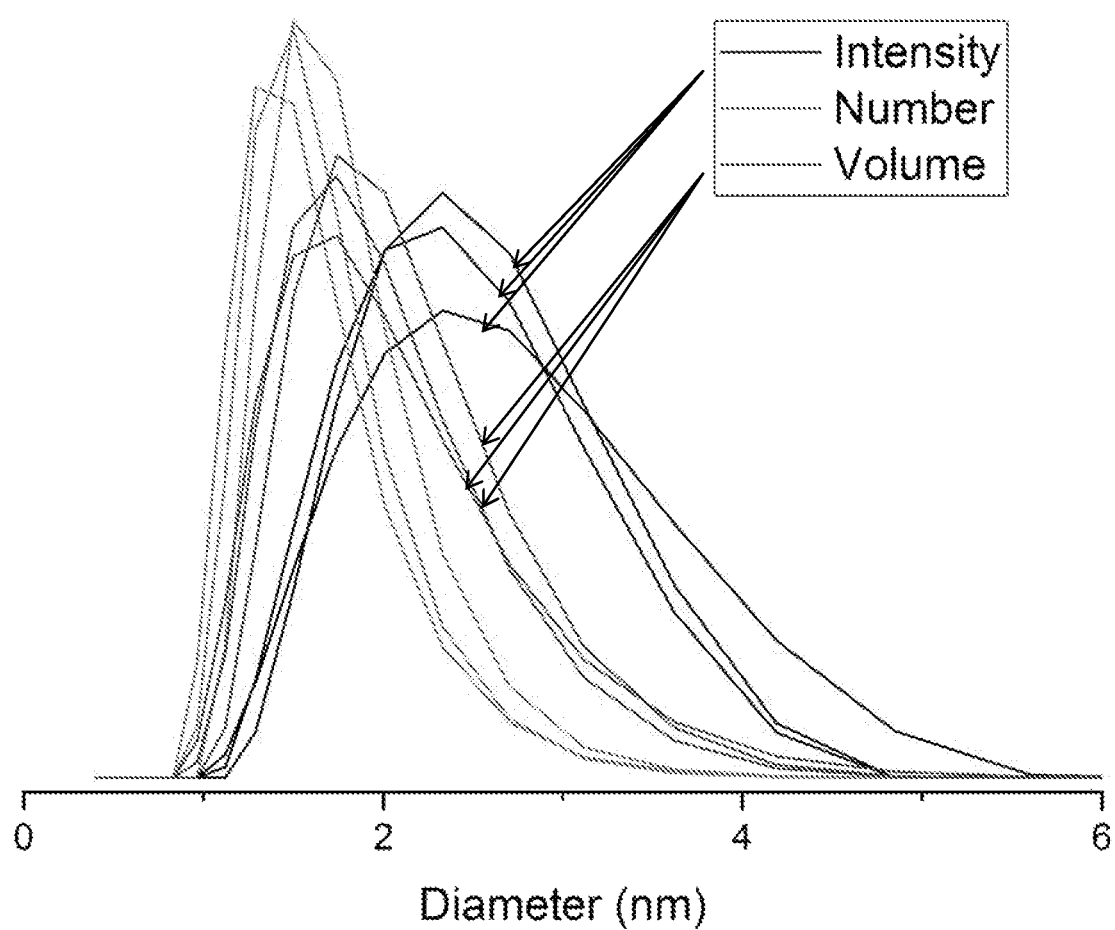
FIG. 3 is a graph showing static light scattering measurements of an aqueous BAC/NH$_4$OH solution prior to the addition of TEOS demonstrating scattering intensity (y-axis) versus particle diameter (x-axis).
Figure 4A:
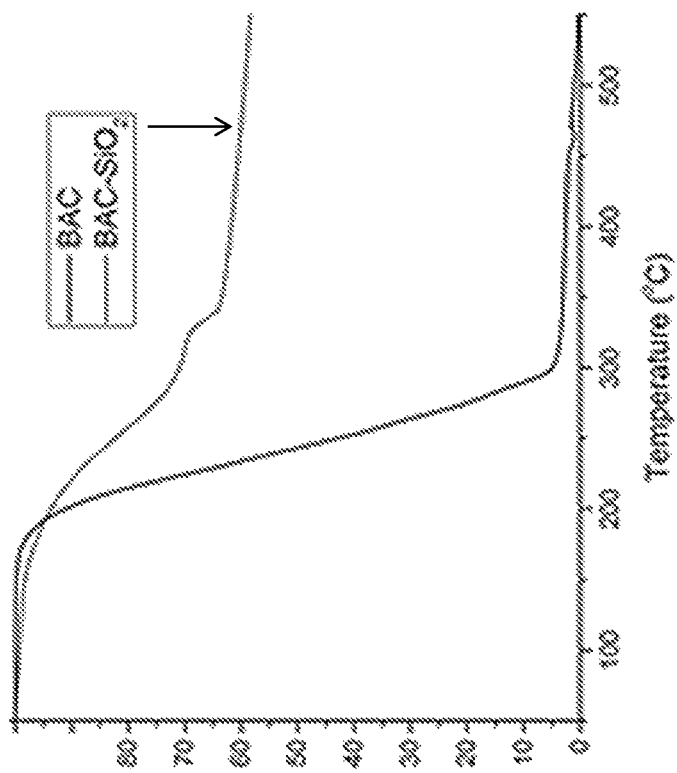
FIG. 4A is a set of attenuated total reflectance Fourier transform infrared (ATR-FTIR) spectra of lyophilized BAC, as-synthesized BAC-SiO$_2$ and calcined BAC-SiO$_2$.

Example 2: Characterization of BAC-Templated Mesostructured Silica Nanoparticles Synchrotron small-angle X-ray scattering (SAXS) and static light scattering (SLS) measurements of aqueous BAC/NH$_4$OH solution prior to TEOS addition revealed the presence of nano-sized BAC micelle aggregates. SAXS profile (FIG. 2) exhibited diffraction peaks within the range of about 20-70 Å. SLS measurements (FIG. 3), in close agreement with SAXS, revealed size distribution of about 10-50 Å. The presence of BAC within the mesoporous silica was confirmed using ATR-FTIR analysis. The FTIR spectra (FIG. 4A) exhibited C—H stretching bands (2854 cm$^{-1}$ and 2924 cm$^{-1}$) and C—H bending vibration band (1457 cm$^{-1}$) present in both the pure BAC and the BAC-SiO$_2$ spectra, which are characteristic of alkylammonium cations. Asymmetric (1044 cm$^{-1}$) and symmetric (809 cm$^{-1}$) Si—O—Si bands were observed in the spectra of BAC-SiO$_2$ before and after calcination.

Figure 4B:
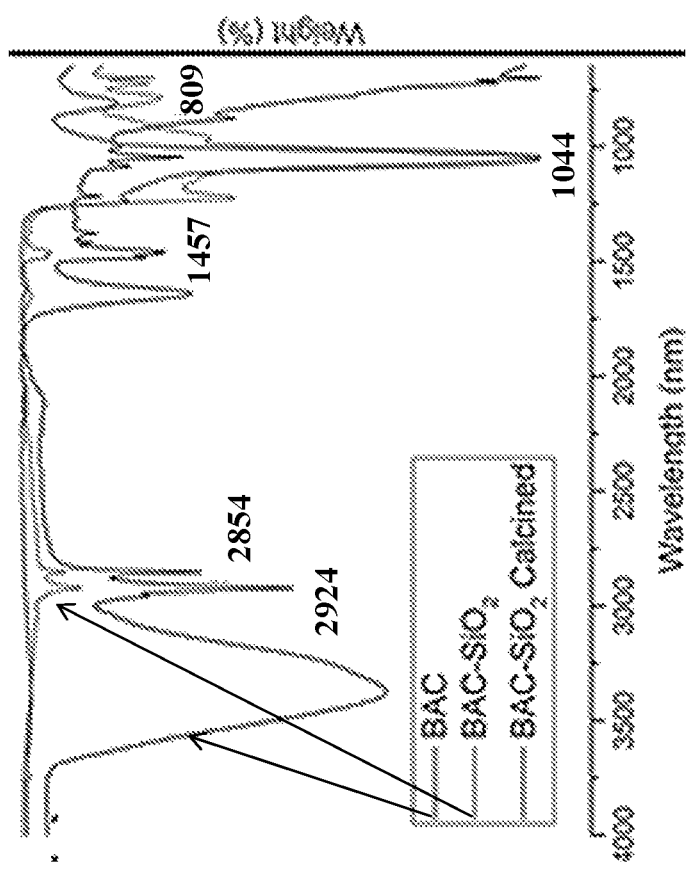
FIG. 4B is a graph showing thermogravimetric analysis (TGA) data plots for lyophiblized BAC (lower line) and as-synthesized BAC-SiO$_2$ (upper line).
Figure 5:
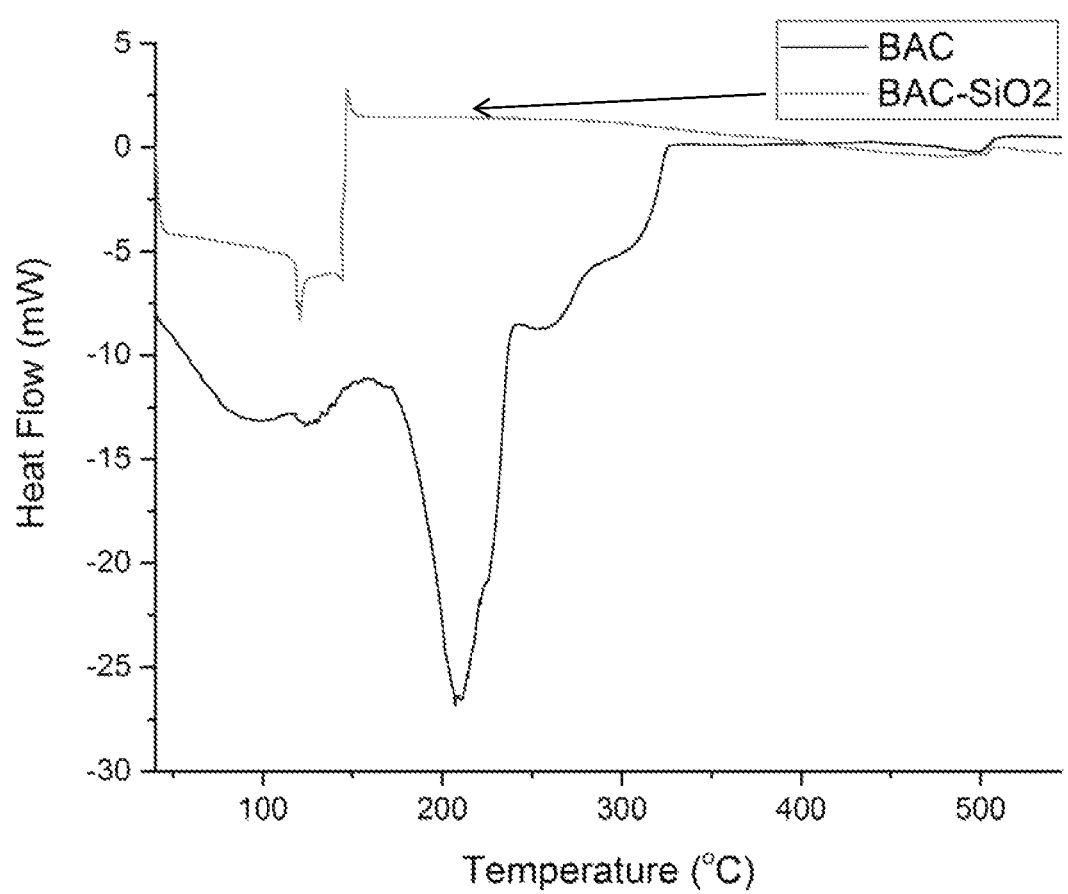
FIG. 5 is a graph showing differential scanning calorimetry (DSC) plots of BAC (lower line) and BAC-SiO$_2$ (upper line).

Quantification of BAC within the framework of the material was conducted using thermogravimetric analysis (TGA). TGA data of freeze-dried BAC showed a 95% weight loss in the range of 170-300° C. due to its thermal degradation (FIG. 4B). The TGA curve of BAC-SiO$_2$ material exhibited four distinct weight loss ranges: 1) the loss of water, and potentially any residual ammonia from the synthesis, at <170° C.; 2) first step of BAC degradation in in the range of 170-300° C.; 3) second step of BAC degradation in the range of 300-340° C.; and 4) loss of water due to the condensation of silanol groups (—SiOH+—SiOH→—Si—O-Si+H$_2$O). The weight loss between 170-340° C. was about 36% (0.56 g per 1 g SiO$_2$), which corresponded to the amount of BAC within the BAC-SiO$_2$ powder. The thermal degradation pathway of encapsulated BAC seems significantly different from "free" BAC, which is consistent with similar studies on cetyltrimethylammonium bromide (CTAB) and alkylamidopropyldimethylbenzylammonium (Miramistin) (Dement'eva, et al., Colloid Journal 2016, 78 (5), 586-595; Dement'eva, et al., RSC Advances 2016, 6 (42), 36207-36210). The major step observed in the TGA of BAC-SiO$_2$ occurred at a lower temperature than the corresponding step with pure BAC. This is consistent with differential scanning calorimetry (DSC) results obtained for the materials (FIG. 5), where the predominant endothermic peak occurred at 120-140° C. and 185-230° C. for BAC-SiO$_2$ and BAC, respectively. A decrease in thermal degradation onset temperature within the silica framework can be explained by the fact that pure BAC exhibits more crystallinity than that of the amorphous BAC phase within the framework. Elemental analysis of BAC-SiO$_2$ before and after calcination at 300° C. for 1 min suggested that the second degradation step at 300-340° C. was due to the decomposition of predominantly aliphatic moieties since nitrogen was not detected. The elemental analysis data suggested that the first step entailed degradation involving the quaternary ammonium while the second step involved degradation of the hydrocarbon moieties. These results are consistent with previous experiments which used temperature-programmed desorption coupled with mass-spectrometric detectors of CTAB encapsulated in a SiO$_2$ matrix. Two different mechanisms of CTAB degradation have been proposed: 1) at lower temperatures (i.e., <250° C.), the encapsulated CTAB molecules degrade predominantly via Hofmann elimination producing hexadecene and trimethylamine; and 2) at higher temperatures (i.e., 250-300° C.), alkyl chain fragmentation becomes essential. The lower temperature degradation step was absent for pure CTAB. Taking into consideration the difference in molecular structures between CTAB and BAC it is reasonable to propose that during the first thermal degradation step below 300° C. (FIG. 4B), BAC undergoes Hofmann elimination to yield dimethylbenzylamine and either dodecene, tetradecene, hexadecane, or octadecene (see molecular structure in FIG. 1).

Different thermal degradation pathways have been observed for quaternary ammonium surfactants encapsulated in mesostructured silica as compared to "free" surfactants. It has been proposed that two forms of template molecules are often present which differ in binding strength to the framework. Sample controlled thermal analysis (SCTA) of a CTAB-templated MCM-41 material suggests two phases of surfactant within the inorganic silica host: the predominant phase which is relatively loosely bound and the minor phase that is more strongly bound. The difference in binding strength of the proposed species can be explained by two theories: 1) partial incorporation of the surfactant's hydrophilic head groups into the silica pore walls during hydrolysis-driven SiO$_2$ formation; and 2) OW ion capture or ion exchange, introduced during the synthesis, with quaternary ammonium counter-ions (e.g., Ci, Br).

Calcination of prepared BAC-SiO$_2$ material at 550° C. for 6 h yielded a mesoporous silica powder whose structure and morphology was characterized using high-resolution transmission electron microscope (HRTEM), small-angle X-ray diffraction (SAXRD), and N$_2$ sorption experiments. TEM micrograph (FIG. 4C) showed seemingly disordered mesopores structures with pore widths on the order of 30-50 Å. The SAXRD pattern (FIG. 4D) was characteristic of an isotropic material that formed layers by virtue of consistent size rather than by extended 1D or 2D periodic arrangements of molecules. No short d-spacing diffraction pattern was observed from aligned molecular species. There was only random packing of nearest neighbor pores that gave rise to a consistent, but isotropic, scattering vector near 32 Å, which is the approximate distance between rows of pores. If the pattern was cubic, then the pore-to-pore centroids are what were measured. However, information gathered from TEM micrographs and expected packing arrangements of random spheres appeared to favor an hcp motif, making the observed value to be $\sqrt{3}/2$ times the average core-to-core distance. Thus, the average core-to-core distance was about 37 Å. By incorporating the Scherrer equation, the domain spacing was determined to be ca. 11 nm, which is consistent with three repeats of the 37 Å spacing.

Figure 6:
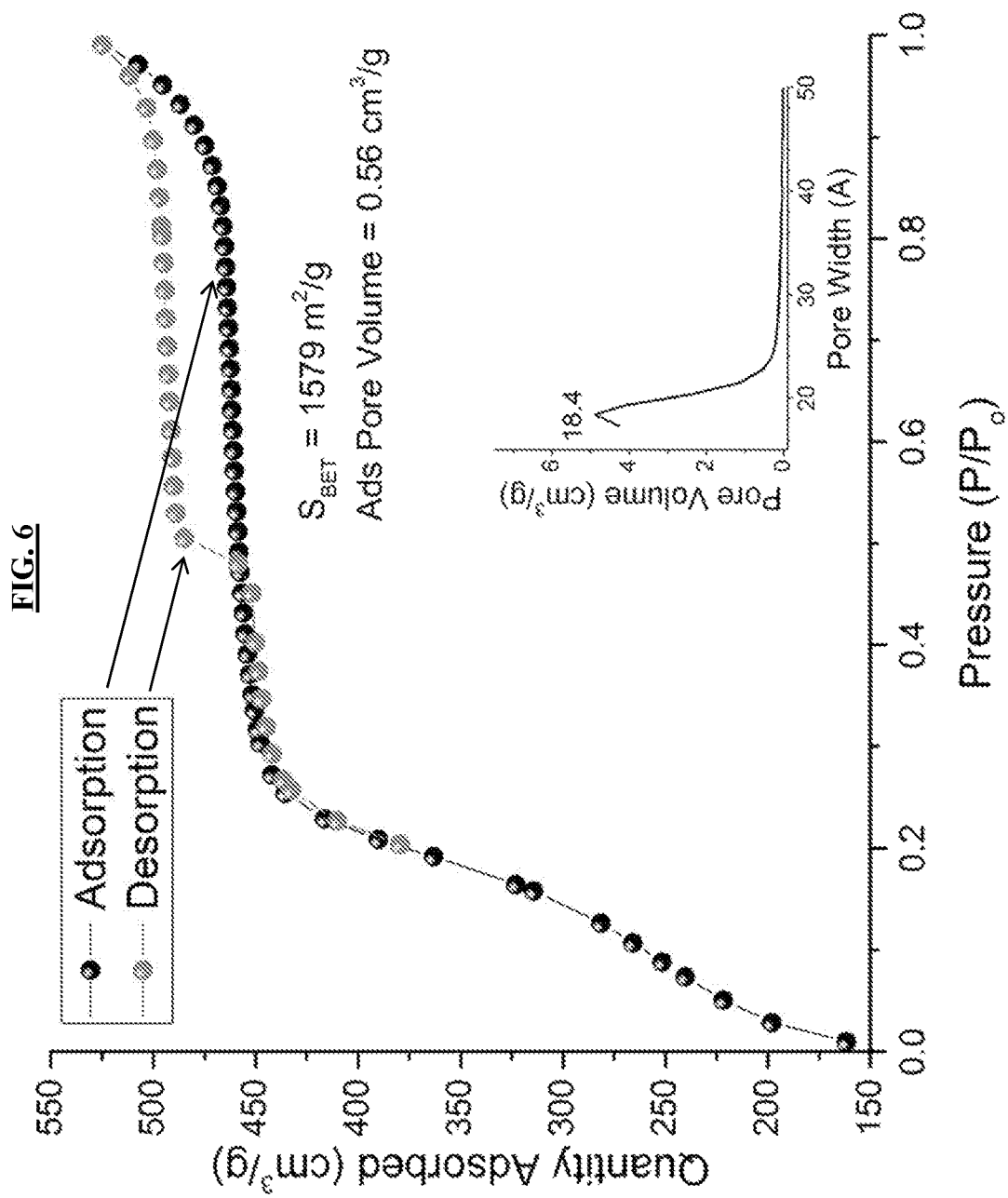
FIG. 6 is a graph showing nitrogen sorption isotherms of calcined BAC-SiO$_2$ measured at 77 K.

The nitrogen sorption results revealed a type IV isotherm (FIG. 6) with capillary condensation at a relative pressure of ca. 0.2 and a well-defined H4 hysteresis loop closing at a pressure of ca. 0.50. By analyzing the data using Brunauer-Emmett-Teller (BET) method and Barrett-Joyner-Halenda (BJH) method, the surface area, pore width, and pore volume were found to be 1579 m$^2$g$^{-1}$, 18.4 Å, and 0.56 cm$^3$g$^{-1}$, respectively. Application of the Kruk-Jaroniec-Sayari (KJS) corrections on the data with cylindrical pore assumptions yielded a pore width closer to 30 Å. The hysteresis loop also suggested the presence of a small proportion of larger mesopores on the order of ~100-500 Å, which is attributed to inter-particle gaps.

Example 3: Mesostructured Silica Nanoparticle Degradation and BAC Release

In solutions with low pH values (1.2), significant and unavoidable interference was observed in the entire UV-Vis range when the BAC-SiO$_2$ was dispersed. This can be attributed to the dissolution of the silica framework and dispersion of nano-scale particles within the medium. Without intending to be limited to any particular theory, this hypothesis is consistent with stability studies of MSNs under acidic conditions where it has been proposed that silica, especially if synthesized under alkaline conditions, undergoes degradation via hydrolysis of Si—O—Si due to protonation of the bridging oxygen concomitant with the conjugate base donating electron density to the silicon atom resulting in SiO bond cleavage (El Mourabit, et al., RSC Advances 2012, 2 (29), 10916-10924.). Because the conjugate base acts as a nucleophile during Si—O—Si cleavage, the composition can play a key role on overall silica matrix degradation. The hydrolysis and subsequent condensation reactions are reversible and are believed to be the driving force responsible for "reprecipitation" of silica matrix during drug release.

Figure 7A:
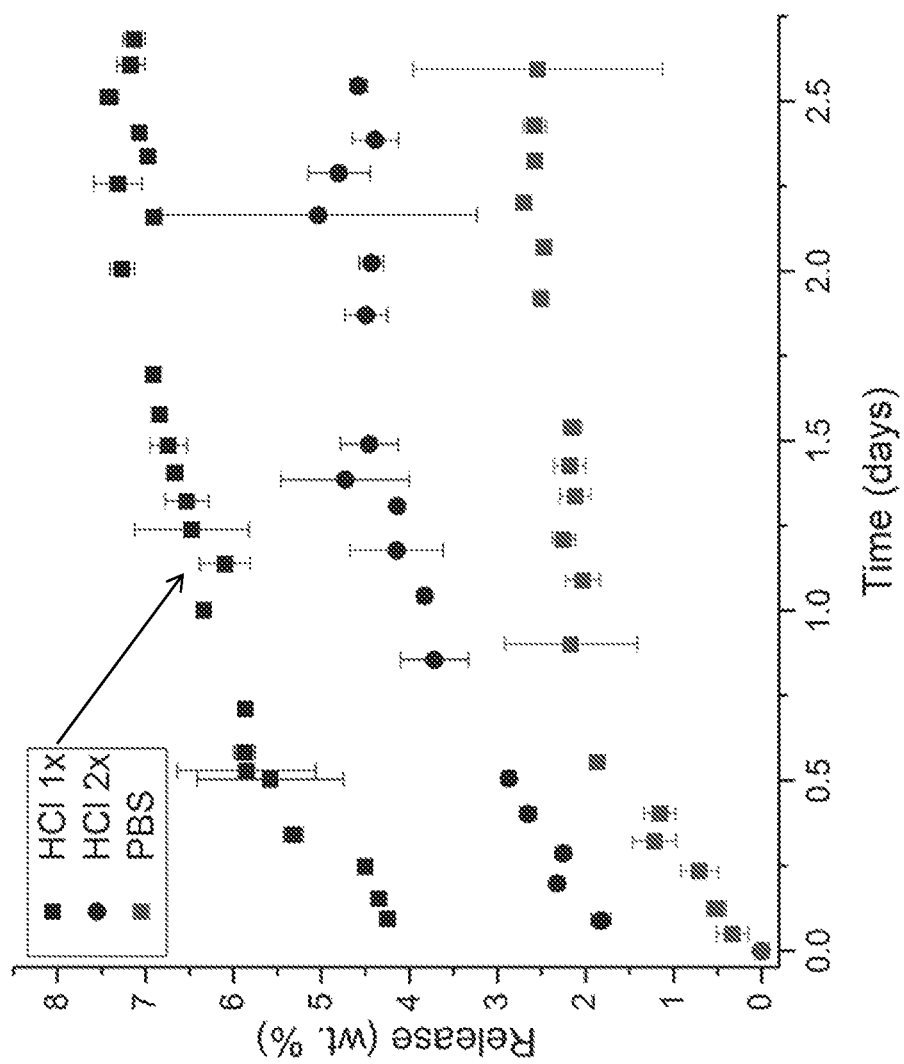
FIG. 7A is a graph showing the release profile of BAC from BAC-SiO$_2$ in HCl solution with pH 4.0 (HCl 1×), second release in fresh HCl solution with pH 4.0 (HCl 2×) and in phosphate-buffered saline (PBS) solution with pH 7.4, along with the corresponding standard deviation.

A kinetic study of BAC release from MSNs into an aqueous solution in static conditions indicates that the release rate strongly depends on the pH. The drug release experiments were carried out using 8 mg/mL of BAC-SiO$_2$ material in room temperature (ca. 24° C.). Intercellular pH of healthy human tissues is 6.8-7.2, but decreases to a pH value of ca. 5 or lower in the presence of inflammation, around tumor sites, or at specific areas of the body (e.g., endosomes, lysosomes, stomach). In solutions with pH of 7.4, only 2.5% of the encapsulated BAC was released within 2-3 days (FIG. 7A). Upon decreasing pH to 4.0, a larger portion of BAC (7.1% of the encapsulated payload) was released within the same time frame. Without wishing to be limited to any particular theory, the increase in BAC release can be largely attributed to the replacement of cationic BAC with protons at the terminal Si—O$^-$ sites. Although the majority (ca. 93%) of the BAC remained within the nanoparticles, a second release profile (FIG. 7A) indicated an additional 4.5% of BAC was released upon placing the material in a fresh solution with pH 4.0. These results suggest that the BAC could continuously release in physiologically-relevant dynamic conditions.

In order to investigate the mechanism of BAC release, the in vitro drug release data was analyzed using the power law (Korsmeyer-Peppas) model (Eq. 1). This model, based on Fick's second law of diffusion for thin films, depicts drug release from polymeric systems with the assumption that the diffusion coefficient was concentration independent and the drug is homogeneously distributed throughout the drug delivery system (DDS). The general form is:

$$\frac{M_t}{M_\infty} = kt^n \qquad \text{Eq. 1}$$

where $M_t$ and $M_\infty$ are the cumulative amounts of released BAC at time t and infinity, respectively, n is the release exponent that characterizes the desorption mechanism, and k is the kinetic constant which correlates directly with the diffusion coefficient, D, if a constant thickness of the diffusion path is assumed. Although the values of n are geometry dependent, the same BAC-SiO$_2$ material was used for the release experiments, thereby eliminating the geometry variable. A plot of log($M_t/M_\infty$) as a function of log(t), with t≤62 h in pH 4.0 and 7.4, (see Drug Release Studies) yielded n values shown in Table 1.

TABLE 1

Analysis of kinetic data for BAC desorption

| Release Media | log ($M_t/M_\infty$) vs. log (t) | n | R |
|---|---|---|---|
| PBS | y = 0.702x − 1.0 | 0.702 ± 0.06 | 0.95 |
| HCl [a] | y = 0.208x − 0.3 | 0.208 ± 0.03 | 0.94 |

[a] pH 4.00

Comparison of n values indicated that there were at least two processes that could govern the release of BAC from the mesostructured silica nanoparticles. In PBS at pH 7.4, n=0.7, which is indicative of non-Fickian diffusion with a superposition of framework swelling or erosion. However, in HCl solution at pH 4.0, n=0.2, which suggests non-Fickian diffusion from disordered pores with respect to shape, length, and diameter. It is noteworthy that the dependence of n values to the release should, in reality, comprise several superimposed processes. For example, penetration of water into the materials is present in the cases of both release media, but it is more profound during release in the PBS environment.

Kinetic modeling of the release data (see Drug Release Studies) demonstrated that the release mechanism in pH 7.4 and 4.0 was different. The proposition of different mechanisms responsible for BAC release in the aforementioned media was reasonable due to the vast differences in the release environment. At pH 7.4, an environment representative of extracellular healthy tissues and blood, the ratio of [OH$^-$]/[H$_3$O$^+$] is 6.3 at 25° C. Thus, the excess OH$^-$ ions have the capacity to interact and exchange with the chloride in BAC. On the other hand, at pH 4.0 [H$_3$O$^+$]/[OH$^-$]=10$^6$ and the terminal silanol (—Si—OH) groups are able to become relatively more protonated. The pK$_a$ of silanol groups is ca. 4-5. During the synthesis of the materials in alkaline solution, cationic SDAs (i.e., BAC) self-assembled with the hydrolyzed silicate precursors to form an ion pair. The electrostatically-bound template molecules can be liberated by either ion exchange with another cation (e.g., H$^+$) or reducing the amount of available silanol sites (e.g., condensation of two silanol groups). Thus, during the drug release in HCl, protonation of the silanol groups or acid-catalyzed condensation of two silanol groups occurs concomitantly with the release of the cationic BAC surfactants. Additionally, the presence of hydrated protons promotes framework cross-linkage, which reduces silanol groups and liberates electrostatically-bound BAC.

Without intending to be limited to any particular theory, it is believed that the rate of release of BAC is governed by two competing processes: 1) gradual dissolution of silica framework by penetrating water molecules and 2) the interaction of the releasing molecules with the silica surface. Thus, the controlled release of the template can be modulated by adjusting synthetic procedures and thereby modifying the resulting composition, structure, and morphology. Biocompatibility and drug release properties rely on various parameters such as size, shape, structure, and synthetic procedures. In certain embodiments, the materials prepared herein exhibit significantly faster degradation rates, and hence improved biocompatibility, as compared to their calcined counterparts. Additionally, as calcination is not applied to the compositions of the invention, the density of surface silanol groups is conserved, allowing for further modification of the silanol groups and/or for the silanol groups to interact with microbes.

Example 4: Antibacterial Effect of BAC Release from BAC-SiO$_2$

The antibacterial effect of BAC release from BAC-SiO$_2$ was tested for eradicating S. aureus and S. enterica, Gram-positive and Gram-negative human bacterial pathogens, respectively. BAC-SiO$_2$ exposure resulted in a time- and concentration-dependent killing of both bacteria (FIG. 7C). Notably, BAC-SiO$_2$ was more effective at killing S. aureus than S. enterica. Without intending to be limited to any particular theory, the difference in effectivity is potentially due to the outer membrane of Gram-negative bacteria providing additional protection from exposure to the BAC. Control SiO$_2$ had no effect on bacterial viability while BAC-SiO$_2$ displayed similar killing potential as pure BAC, taking into account the amount of BAC present in the BAC-SiO$_2$ (BAC-SiO$_2$ was 40% BAC by weight as tested)

Figure 7B:
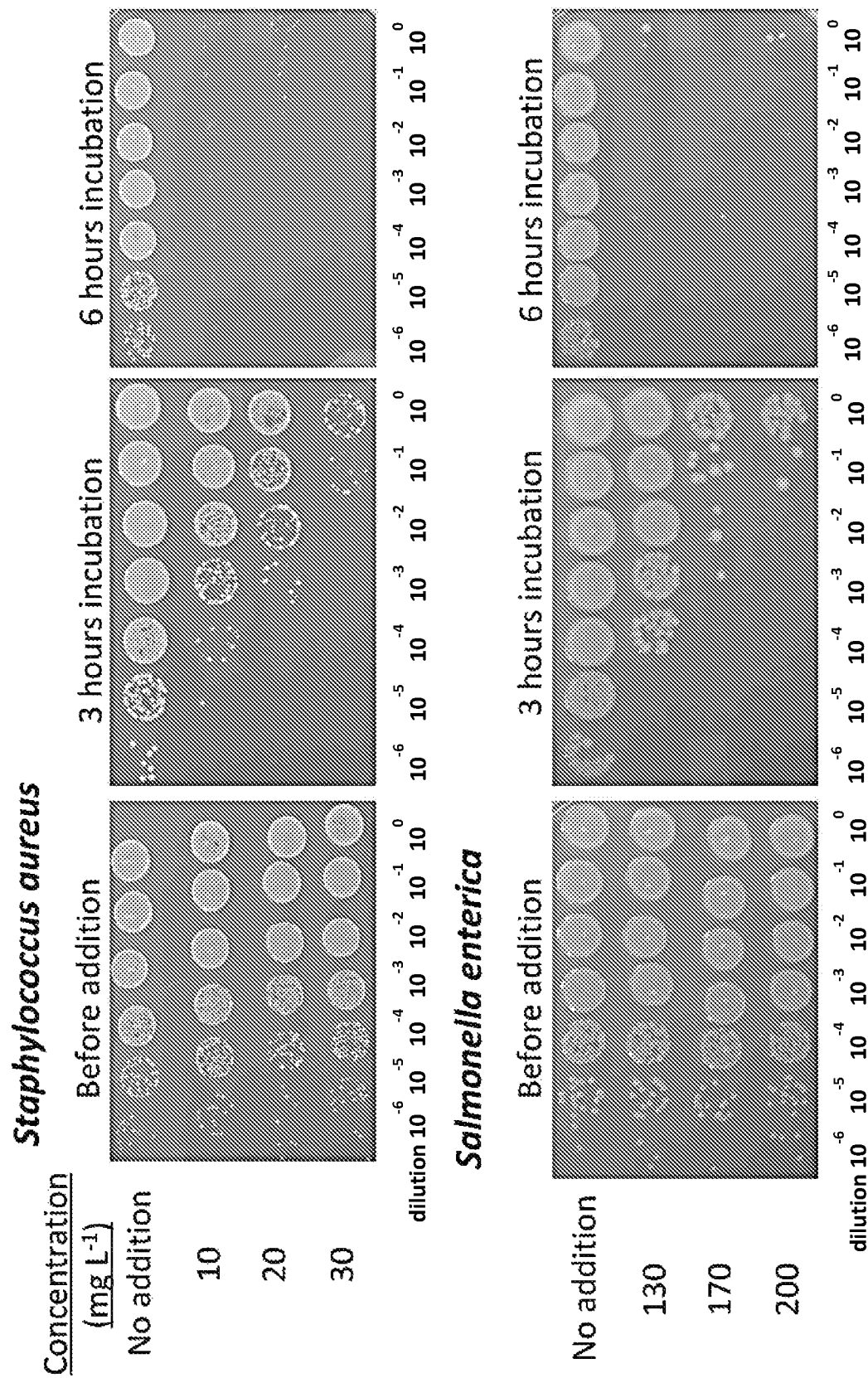
FIG. 7B is a set of photographs showing time and dose-dependent killing of *S. aureus* and *S. enterica* by BAC-SiO$_2$. Bacterial killing was monitored in biological triplicates and representative photos of drop plates containing serial dilutions of treated cultures are displayed.
Figure 7C:
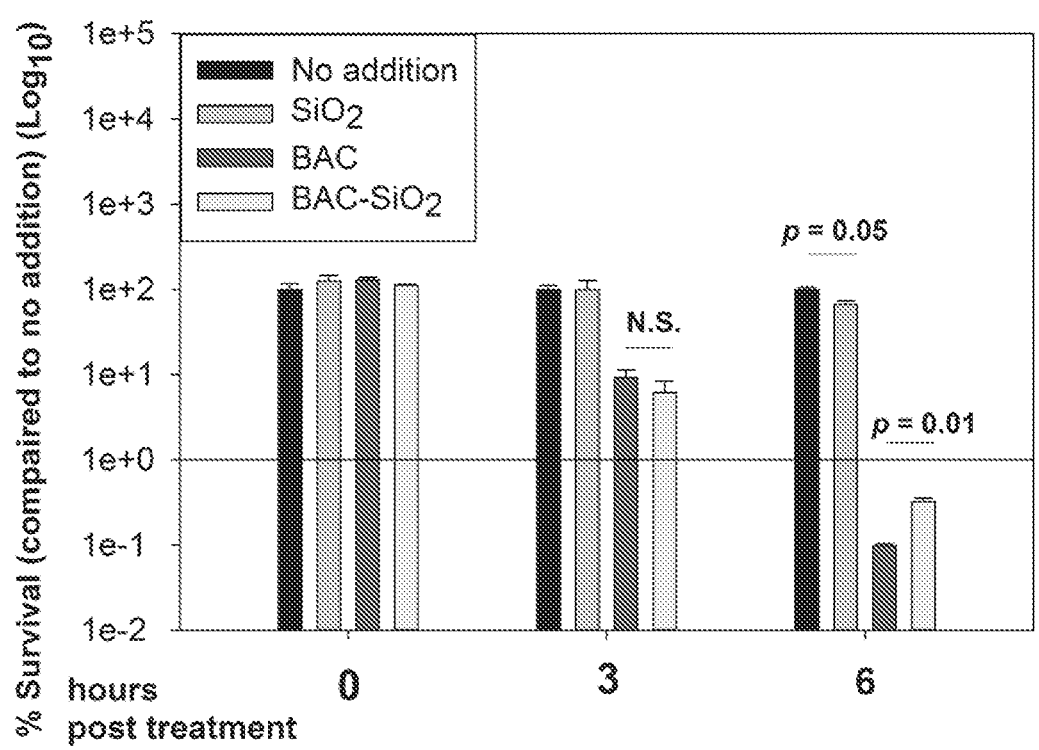
FIG. 7C is a graph showing percentage of *S. aureus* survival upon exposure to 12 mg L$^{-1}$ SiO$_2$, 4 mg L$^{-1}$ BAC, or 10 mg L$^{-1}$ BAC-SiO$_2$ for 0, 3, and 6 hours. Bacterial killing was monitored in biological triplicates. The average survival is displayed, and error bars represent standard deviations. Statistical significance was calculated using a two-tailed t-test with significant p-values displayed. "N.S." denotes "not significant".

(FIG. 7B). These results suggest that a) the addition of BAC-SiO$_2$ to liquid growth medium results in BAC release leading to bacterial killing, and b) that BAC-SiO$_2$ is as effective at killing *S. aureus* as pure BAC.

ENUMERATED EMBODIMENTS

The following exemplary embodiments are provided, the numbering of which is not to be construed as designating levels of importance.

Embodiment 1 provides a composition comprising mesostructured silica particles and benzalkonium chloride, wherein the mesostructured silica particles comprise pores, wherein the benzalkonium chloride is embedded within the pores of the mesostructured silica particles, and wherein the silica particles are at least one selected from silica nanoparticles and/or silica microparticles.

Embodiment 2 provides the composition of Embodiment 1, wherein the composition comprises at least about 1% (w/w) benzalkonium chloride.

Embodiment 3 provides the composition of any of Embodiments 1-2, wherein the composition comprises at least about 30% (w/w) benzalkonium chloride.

Embodiment 4 provides the composition of any of Embodiments 1-3, wherein the composition comprises about 34-40% (w/w) benzalkonium chloride.

Embodiment 5 provides the composition of any of Embodiments 1-4, wherein at least a fraction of the mesostructured silica particles have a surface area of about 1,000 m$^2$/g to about 2,000 m$^2$/g.

Embodiment 6 provides the composition of any of Embodiments 1-5, wherein at least a fraction of the mesostructured silica particles have a surface area of about 1,500 m$^2$/g.

Embodiment 7 provides the composition of any of Embodiments 1-6, wherein the mesostructured silica particles comprise pores having an average diameter of about 10 Å to about 200 Å.

Embodiment 8 provides the composition of any of Embodiments 1-7, wherein the mesostructured silica particles comprise pores having an average diameter of about 30 Å to about 50 Å.

Embodiment 9 provides the composition of any of Embodiments 1-8, wherein the mesostructured silica particles comprise pores having an average volume of about 0.1 cm$^3$/g to about 1.0 cm$^3$/g.

Embodiment 10 provides the composition of any of Embodiments 1-9, wherein the mesostructured silica particles have an average diameter of about 50 nm to about 1.00 nm.

Embodiment 11 provides the composition of any of Embodiments 1-10, further comprising at least one swelling agent.

Embodiment 12 provides the composition of Embodiment 11, wherein the at least one swelling agent is selected from 1,3,5-trimethylbenzene (TMB), polypropylene glycol) (PPG), decane, octane, 1,3,5-triisopropylbenzene, and/or hexane.

Embodiment 13 provides the composition of any of Embodiments 1-12, further comprising at least one additional pharmaceutical agent.

Embodiment 14 provides the composition of Embodiment 13, wherein the at least one pharmaceutical agent is at least one selected from an analgesic agent, an anti-inflammatory agent, an antimicrobial agent, an antiviral agent, an antifungal agent, an anti-pruritic, an antiperspirant, a sunblocking agent, a vitamin, an NSAID, a skin cleanser, a disinfectant, a corticosteroid, a protein, a peptide, and/or a hormone.

Embodiment 15 provides the composition of any of Embodiments 13-14, wherein the at least one pharmaceutical agent is selected from ethanol, folic acid, salicylic acid, benzoic acid, hydrocortisone, vitamin A and derivatives and analogues thereof, vitamin D and derivatives and analogues thereof, clindamycin, mupirocin, acyclovir, and/or clobetasol propionate.

Embodiment 16 provides the composition of any of Embodiments 1-15, which is an antimicrobial composition.

Embodiment 17 provides the composition of any of Embodiments 1-16, which is a pharmaceutically acceptable composition.

Embodiment 18 provides the composition of any of Embodiments 1-17, which is formulated for topical administration.

Embodiment 19 provides the composition of any of Embodiments 1-18, which is incorporated into one or more selected from a wound dressing, a lotion, an ointment, a gel, a powder, a spray, an aqueous solution, and/or an anhydrous solution.

Embodiment 20 provides the composition of any of Embodiments 1-19, which is formulated for use as a cleaning agent, a disinfecting agent, a preserving agent, a bacteriostatic agent, an antifungal agent, and/or an antiviral agent.

Embodiment 21 provides the composition of any of Embodiments 1-20, which is formulated as part of at least one selected from an antimicrobial coating, an antifungal coating, and/or an antiviral coating.

Embodiment 22 provides a method of making the composition of any of Embodiments 1-21, the method comprising heating an aqueous solution comprising BAC, a base and a silica precursor, and collecting the mesostructured silica particles through at least one method selected from filtering the solution and/or centrifuging the solution.

Embodiment 23 provides the method of Embodiment 22, wherein the aqueous solution is heated to about 80° C.

Embodiment 24 provides the method of any of Embodiments 22-23, wherein the aqueous solution is heated for about 5 min to about 72 h.

Embodiment 25 provides the method of any of Embodiments 22-24, wherein the collected mesoporous silica nanoparticles are dried after filtration or centrifugation.

Embodiment 26 provides the method of any of Embodiments 22-25, wherein the silica precursor is added dropwise to a mixture of BAC and the base to form the aqueous solution.

Embodiment 27 provides the method of any of Embodiments 22-26, wherein the BAC and silica precursor are present in a molar ratio of about 1:10 to about 1:100.

Embodiment 28 provides the method of any of Embodiments 22-27, wherein the aqueous solution is alkaline.

Embodiment 29 provides the method of any of Embodiments 22-28, wherein the base is at least one base selected from ammonium hydroxide (NH$_4$OH), Na$_2$CO$_3$, NEt$_3$, lysine, NaOH, and/or KOH.

Embodiment 30 provides the method of any of Embodiments 22-29, wherein the silica precursor material is at least one selected from tetraethyl orthosilicate (TEOS), sodium silicate, tetramethyl orthosilicate (TMOS), tetrapropyl orthosilicate (TPOS), tetrabutyl orthosilicate (TBOS), silicic acid, sodium silicate, and/or ammonium hexafluorosilicate ((NH$_4$)$_2$SiF$_6$).

Embodiment 31 provides the method of any of Embodiments 22-30, wherein the aqueous solution further comprises a silica mineralizer.

Embodiment 32 provides the method of any of Embodiments 22-31, wherein the silica mineralizer is a fluoride salt.

The disclosures of each and every patent, patent application, and publication cited herein are hereby incorporated herein by reference in their entirety. While this invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations.

What is claimed is:

1. A composition comprising mesostructured silica particles and benzalkonium chloride, wherein each of the following applies:
   (a) the mesostructured silica particles comprise pores;
   (b) wherein the benzalkonium chloride is the only surfactant embedded within the pores of the mesostructured silica particles;
   (c) each silicon atom in the silica particles is covalently bonded only to oxygen atoms; and
   (d) the silica particles are at least one selected from silica nanoparticles and silica microparticles.

2. The composition of claim 1, wherein the composition comprises at least about 1% (w/w) benzalkonium chloride.

3. The composition of claim 2, wherein the composition comprises at least about 30% (w/w) benzalkonium chloride.

4. The composition of claim 3, wherein the composition comprises about 34-40% (w/w) benzalkonium chloride.

5. The composition of claim 1, wherein at least one of the following applies:
   (a) a fraction of the mesostructured silica particles have a surface area of about 1,000 $m^2$/g to about 2,000 $m^2$/g;
   (b) the mesostructured silica particles comprise pores having an average diameter of about 10 A to about 200 A;
   (c) the mesostructured silica particles comprise pores having an average volume of about 0.1 $cm^3$/g to about 1.0 $cm^3$/g; and
   (d) the mesostructured silica particles have an average diameter of about 50 nm to about 1,000 nm.

6. The composition of claim 5, wherein at least one of the following applies:
   (a) a fraction of the mesostructured silica particles have a surface area of about 1,500 $m^2$/g; and
   (b) the mesostructured silica particles comprise pores having an average diameter of about 30 A to about 50 A.

7. The composition of claim 1, further comprising at least one swelling agent.

8. The composition of claim 7, wherein the at least one swelling agent is selected from 1,3,5-trimethylbenzene (TMB), decane, octane, 1,3,5-triisopropylbenzene, and/or hexane.

9. The composition of claim 1, further comprising at least one additional pharmaceutical agent.

10. The composition of claim 9, wherein the at least one pharmaceutical agent is at least one selected from an analgesic agent, an anti-inflammatory agent, an antimicrobial agent, an antiviral agent, an antifungal agent, an antipruritic, an antiperspirant, a sunblocking agent, a vitamin, an NSAID, a skin cleanser, a disinfectant, a corticosteroid, a protein, a peptide, and/or a hormone.

11. The composition of claim 9, wherein the at least one pharmaceutical agent is selected from ethanol, folic acid, salicylic acid, benzoic acid, hydrocortisone, vitamin A, vitamin D, clindamycin, mupirocin, acyclovir, and/or clobetasol propionate.

12. The composition of claim 1, which is an antimicrobial composition.

13. The composition of claim 1, which is a pharmaceutically acceptable composition.

14. The composition of claim 13, which is formulated for topical administration.

15. The composition of claim 13, which is incorporated into one or more selected from a wound dressing, a lotion, an ointment, a gel, a powder, a spray, an aqueous solution, and/or an anhydrous solution.

16. The composition of claim 1, which is formulated either:
   (a) for use as a cleaning agent, a disinfecting agent, a preserving agent, a bacteriostatic agent, an antifungal agent, and/or an antiviral agent; or
   (b) as part of at least one selected from an antimicrobial coating, an antifungal coating, and/or an antiviral coating.

17. A method of making a composition comprising mesostructed silica particles and a benzalkonium chloride, wherein each of the following applies: (a) the mesostructured silica particles comprise pores; (b) the benzalkonium choloride is the only surfactant embedded within the pores of the mesostructured silica particles; (c) each silicon atom in the silica particles is covalently bonded only to oxygen atoms; and (d) the silica particles are at least one selected from silica nanoparticles and silica microparticles,
   the method comprising heating an aqueous solution comprising benzalkonium chloride as the only surfactant, a base, and a silica precursor, and collecting the mesostructured silica particles through at least one method selected from filtering the solution and/or centrifuging the solution.

18. The method of claim 17, wherein at least one of the following applies:
   (a) the aqueous solution is heated to about 80° C.;
   (b) the aqueous solution is heated for about 5 min to about 72 h;
   (c) the collected mesostructured silica particles are dried after filtration or centrifugation;
   (d) the silica precursor is added dropwise to a mixture of benzalkonium chloride and the base to form the aqueous solution;
   (e) the benzalkonium chloride and silica precursor are present in a molar ratio of about 1:10 to about 1:100; the aqueous solution is alkaline;
   (g) the base is at least one base selected from the group consisting of ammonium hydroxide ($NH_4OH$), $Na_2CO_3$, $NEt_3$, lysine, NaOH, and KOH; and
   (h) the silica precursor material is at least one selected from tetraethyl orthosilicate (TEOS), sodium silicate, tetramethyl orthosilicate (TMOS), tetrapropyl orthosilicate (TPOS), tetrabutyl orthosilicate (TBOS), silicic acid, and sodium silicate.

19. The method of claim 17, wherein the aqueous solution further comprises a silica mineralizer.

20. The method of claim 19, wherein the silica mineralizer is a fluoride salt.

* * * * *